US010967135B2

(12) United States Patent
Deck

(10) Patent No.: US 10,967,135 B2
(45) Date of Patent: Apr. 6, 2021

(54) METHOD AND DEVICE FOR REMOVING GAS AND/OR GAS BUBBLES FROM A LIQUID MEDICAMENT STORED IN A RESERVOIR

(71) Applicant: Roche Diabetes Care, Inc., Indianapolis, IN (US)

(72) Inventor: Frank Deck, Niederkirchen (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 235 days.

(21) Appl. No.: 15/880,196

(22) Filed: Jan. 25, 2018

(65) Prior Publication Data

US 2018/0214642 A1 Aug. 2, 2018

(30) Foreign Application Priority Data

Jan. 31, 2017 (EP) ...................... 17153976

(51) Int. Cl.
*A61M 5/36* (2006.01)
*A61M 5/14* (2006.01)
*A61M 5/145* (2006.01)
*B01F 11/00* (2006.01)

(52) U.S. Cl.
CPC ............... *A61M 5/36* (2013.01); *A61M 5/14* (2013.01); *A61M 5/1452* (2013.01); *B01F 11/0071* (2013.01); *A61M 2005/1403* (2013.01); *B01F 2215/0034* (2013.01)

(58) Field of Classification Search
CPC ............ A61M 5/36; A61M 2005/1402; A61M 2209/045; A61J 1/20; A61J 1/2051; A61J 1/2096
See application file for complete search history.

(56) References Cited

U.S. PATENT DOCUMENTS 5,533,981 A * 7/1996 Mandro .............. A61M 5/1456
604/208
9,138,534 B2 * 9/2015 Yodfat ................ F04B 43/1269
2008/0269713 A1 10/2008 Kavazov
(Continued)

FOREIGN PATENT DOCUMENTS

EP 2 229 970 A1 9/2010
EP 2 295 096 A1 3/2011
(Continued)

OTHER PUBLICATIONS

Extended European Search Report for EP 17153976, dated Jul. 20, 2017, 7 pages.

*Primary Examiner* — Laura A Bouchelle

(74) *Attorney, Agent, or Firm* — Bose McKinney & Evans LLP

(57) ABSTRACT

This disclosure concerns a method for removing gas and/or gas bubbles from a liquid medicament stored in a reservoir for an infusion pump device. The reservoir comprises a displacing member which is at least partly displaceable relative to the reservoir thereby enabling receiving mechanical oscillations in order to generate mechanical waves in the liquid medicament. The method comprises: providing the reservoir; and transmitting a mechanical oscillation to the displacing member of the reservoir thereby generating a mechanical wave in the liquid medicament for removing gas and/or gas bubbles from the liquid medicament.

15 Claims, 5 Drawing Sheets

(56) References Cited

U.S. PATENT DOCUMENTS

2012/0289900 A1 11/2012 Chong et al.
2015/0122338 A1* 5/2015 Hunter .............. A61M 5/16859
                                                                                       137/2

FOREIGN PATENT DOCUMENTS

| EP | 2 455 126 A1 | 5/2012 | |
|---|---|---|---|
| WO | WO 2006/048114 A1 | 5/2006 | |
| WO | WO-2016181384 A2 * | 11/2016 | ........ A61M 5/14244 |

* cited by examiner

METHOD AND DEVICE FOR REMOVING GAS AND/OR GAS BUBBLES FROM A LIQUID MEDICAMENT STORED IN A RESERVOIR

RELATED APPLICATIONS

This application claims priority to EP 17153976.0, filed Jan. 31, 2017, the entire disclosure of which is hereby incorporated herein by reference.

BACKGROUND

This disclosure relates to a method and an auxiliary device for removing gas and/or gas bubbles from a liquid medicament stored in a reservoir for an infusion pump device.

In the therapy of diseases, infusion pump devices can provide for the administration of liquid medicaments to a patient. For example, an infusion pump device in the form of an insulin pump can provide for the administration of insulin to a patient suffering from diabetes. An infusion pump device can comprise a reservoir for storing the liquid medicament. In some applications, reservoirs of infusion pumps are also referred to as cartridges, containers, etc. A reservoir of an infusion pump can be designed to be filled and/or refilled with a liquid medicament according to the needs of the patient. For the purpose of filling or refilling a reservoir of an infusion pump device, the patient can have access to a cooled storeroom having stored storage containers. Each storage container can have stored a particular liquid medicament. The cooled storeroom can have the design of a refrigerator. Storage containers can have the design of vials, storage tanks, storage bottles, etc. Shortly before the patient needs to fill or refill a reservoir of an infusion pump device, the patient withdraws a storage container having the desired liquid medicament from the storeroom, heats the storage container to ambient temperature and fills or refills the reservoir of the infusion pump device with the liquid medicament from the storage container.

A reservoir of an infusion pump device can have various designs and can comprise various materials. For example, a reservoir can have a cylindrical design with a hollow body having two openings. The openings can be arranged at opposite sides of the cylindrical reservoir. At one of the openings, a septum can be arranged for covering, closing, etc. the opening of the reservoir. The other of the openings can support a plunger. The plunger can be movable in an axial direction of the cylindrical reservoir. The plunger can fit tightly in the cylindrical reservoir. The plunger can be moveably arranged for the purpose of filling and/or refilling the reservoir with the liquid medicament as well as for the purpose of administering the liquid medicament to the patient. The reservoir of an infusion pump device can be manufactured out of glass, for example in accordance to the standard DIN ISO 13926 which specifies glass cylinders (part 1), plunger stoppers (part 2), and seals (part 3) for pen-injectors for medical use.

When filling or refilling a reservoir with a liquid medicament from a storage container, it is very important that the reservoir remains without gas or gas bubbles, such as air or air bubbles, because gas or gas bubbles can have various negative effects. Gas or gas bubbles inside the reservoir can have a negative effect on the precision of an administered dosage of the liquid medicament. Gas or gas bubbles inside the reservoir can negatively influence the fluidic stiffness within the infusion pump device, due to the higher compressibility of gas or gas bubbles in relation to the compressibility of liquid medicaments. Gas or gas bubbles in the reservoir can have negative effects on the stability, effectiveness, etc. of the liquid medicament and can negatively influence the lifetime of the liquid medicament. Moreover, administering the liquid medicament to the patient together with gas or gas bubbles can have a negative effect on the patient's health conditions.

Methods are known for removing gas or gas bubbles from a reservoir, which were generated in the reservoir, for example, during transfer of the liquid medicament from the storage container to the reservoir. In a variant, gas bubbles can be removed in a procedure comprising the steps of separation and back transfer. In a step of separation, the reservoir is usually tapped for example with a fingernail, or the reservoir is slightly hammered to the edge of a table plate, wherein the vibrations have the effect that the gas bubbles rise to the top of the reservoir and are separated from the liquid medicament. In a step of back transfer, the gas or gas bubbles can be transferred back to the storage container or elsewhere, for example by slightly moving the plunger.

EP2229970 discloses a bubble trap for removing bubbles from a stream of liquid in an infusion pump device. The bubble trap comprises a grate arranged in the stream. The grate is adapted to retain bubbles that are drifting in the stream. The grate comprises a grate wall and two or more inlets arranged on the grate wall. The stream of liquid can pass the grate through the inlets. The shape and the distribution of the inlets is designed such that a bubble larger than a certain minimum size cannot pass the grate without coming into contact with an inlet. Preferably the shape and the distribution of the inlets is designed such that a bubble below a certain maximum size that is retained in the grate can block only a part of the gross cross-sectional area of the arrangement of inlets.

EP2295096 discloses micro-fluidic chambers for use in a liquid medicament delivery system. A micro-fluidic chamber has a bottom substrate and a top cover spaced from the bottom substrate so as to define a height of the chamber. Walls or fillings are positioned in the chamber and define a fluid channel that extends from an inlet of the chamber to an outlet. The walls or fillings have a height that is less the height of the chamber so as to define a gap between a top surface of the walls or fillings and the top cover. The gap is designed such that it is filled by capillary forces with liquid when liquid is introduced into the fluid chamber. The top cover can be a gas-permeable membrane. Gas in a gas bubble moving along the fluid channel passes the membrane. Gas solved in the liquid migrates into the gap and permeates through the membrane.

EP2455126 discloses a container for storing a medical or pharmaceutical liquid. The container comprises a storage compartment for storing the liquid. The storage compartment comprises an inlet opening for filling the storage compartment and an outlet opening for discharging liquid out of the storage compartment. A hydrophilic membrane is arranged within the storage compartment, which is gas-tight in a wet condition and which at least covers the outlet opening and which contacts the liquid stored in the storage compartment.

As described above, reservoirs can include materials such as glass. When applying methods for removing gas or gas bubbles from a glass reservoir, particular precautions as regards the fragility of the glass material have to be followed. For example, strokes to the glass reservoir or the falling of the glass reservoir to the floor may cause invisible micro-cracks in the glass reservoir, which may cause the glass reservoir to burst apart during the administration of a liquid medicament when used with an infusion pump device. Therefore, operating instructions for glass reservoirs require that a glass reservoir must be replaced if it has been dropped to the floor. Moreover, because of the fragility of glass, applying mechanical strokes or tape to the glass reservoir, for example in order to separate gas bubbles, is strictly forbidden. Stroking the glass reservoir to the edge of a table plate as well as tapping the glass reservoir with a hard piece is equally critical. However, because of properties of glass as regards stiffness and hardness, procedures involving stroking or tapping the glass reservoir would be particularly adapted for separating gas bubbles from the liquid medicament.

WO2006048114 relates to a device for filling or re-filling a container for an infusion fluid. The device comprises a receptacle for the container and a suction device for sucking an infusion fluid into the container. The suction device is actuated by a motor. The device includes a vibratory driving unit for vibrating the container and separating gas bubbles from the infusion fluid. The vibratory driving unit is connected to the container and vibrates the container.

SUMMARY

This disclosure provides a method and an auxiliary device for removing gas and/or gas bubbles from a liquid medicament stored in a reservoir for an infusion pump device, which do not have at least some of the disadvantages of the prior art. In particular, the auxiliary device for removing gas and/or gas bubbles from a liquid medicament stored in a reservoir for an infusion pump reduces mechanical stress to the reservoir. This disclosure provides a method and an auxiliary device for removing gas and/or gas bubbles from a liquid medicament stored in a reservoir for an infusion pump device, which reduce the risk of micro-cracks in the reservoir.

According to this disclosure, the above-mentioned advantages are particularly achieved by a method for removing gas and/or gas bubbles from a liquid medicament stored in a reservoir for an infusion pump device, wherein the reservoir comprises a displacing member which is at least partly displaceable relative to the reservoir, thereby enabling receiving mechanical oscillations in order to generate mechanical waves in the liquid medicament, the method comprising: providing the reservoir; and transmitting a mechanical oscillation to the displacing member of the reservoir thereby generating a mechanical wave in the liquid medicament for removing gas and/or gas bubbles from the liquid medicament. At least a part of the mechanical oscillations received by the displacing member are not transmitted to the reservoir and mechanical stress to the reservoir is therefore reduced compared to mechanical stress resulting in the methods according to prior art, in which methods mechanical forces are directly applied to the reservoir. Hence, the risk of micro-cracks in the reservoir is reduced.

In an embodiment, a reservoir is provided in which the displacing member of the reservoir is a plunger which is arranged displaceable relative to the reservoir at an opening of the reservoir, and wherein the mechanical oscillation is transmitted to the plunger which generates the mechanical wave in the liquid medicament for removing gas and/or gas bubbles from the liquid medicament. In many applications, reservoirs comprise a plunger which is designed for filling the reservoir and which is designed for administering the liquid medicament to the patient. By applying the mechanical oscillation to the plunger, in existing reservoirs gas and/or gas bubbles can be removed from the liquid medicament while reducing mechanical stress to the reservoirs, and while reducing the risk of micro-cracks in the reservoirs.

In an embodiment, a reservoir is provided in which the plunger of the reservoir comprises a sealing element. The sealing element can be arranged between the plunger and the reservoir in order to provide a fluid tight sealing. The sealing element can be designed such that transmission of mechanical oscillations between the plunger and the body of the reservoir are reduced. For example, the sealing element can be designed such that friction forces with the reservoir are reduced. For example, the sealing element can have a flexible design reducing transmission of mechanical forces to the reservoir.

In an embodiment, a reservoir is provided in which a plunger rod is connected to the plunger, wherein the mechanical oscillation is transmitted to the plunger via the plunger rod. Existing reservoirs often comprise a plunger connected to a plunger rod. By applying the mechanical oscillation to the plunger via the plunger rod, in existing reservoirs gas and/or gas bubbles can be removed from the liquid medicament while reducing mechanical stress to the reservoirs, and while reducing the risk of micro-cracks in the reservoirs.

In an embodiment, a reservoir is provided in which the displacing member is a flexible membrane which seals an opening of the reservoir, and wherein the mechanical oscillation is transmitted to the flexible membrane which generates the mechanical wave in the liquid medicament for removing gas and/or gas bubbles from the liquid medicament. For example, a reservoir is provided in which the flexible membrane is a septum. Existing reservoirs often comprise a flexible membrane such as a septum. Due to its flexibility, the flexible membrane is at least partly displaceable relative to the reservoir. By applying the mechanical oscillation to the flexible membrane, in existing reservoirs gas and/or gas bubbles can be removed from the liquid medicament while reducing mechanical stress to the reservoirs, and while reducing the risk of micro-cracks in the reservoirs.

In an embodiment, a reservoir is provided which has a cylindrical design, wherein the displacing member is displaceable in an axial direction of the reservoir. Existing reservoirs have often a cylindrical design with a displacing member such as a plunger, a flexible membrane, a septum, etc. which is displaceable in axial direction of the reservoir. Accordingly, in existing reservoirs gas and/or gas bubbles can be removed from the liquid medicament while reducing mechanical stress to the reservoirs, and while reducing the risk of micro-cracks in the reservoirs.

In an embodiment, the mechanical oscillation has the form of an impulse and/or is the result of a mechanical stroke. The form of an impulse or a mechanical oscillation which results from a mechanical stroke generate a mechanical wave in the liquid medicament comprising high frequencies, thereby enabling that gas and/or gas bubbles separate from the liquid medicament and rise to a top surface of the liquid medicament.

In an embodiment, the mechanical oscillation is such that the mechanical wave generated by the displacing member has the form of a positive pressure wave. A positive pressure wave effects that gas and/or gas bubbles sticking to a shell of the reservoir can be detached from the shell and therefore can rise to the top surface of the liquid medicament.

In an embodiment, the mechanical oscillation is such that the mechanical wave generated by the displacing member has the form of a negative pressure wave. A negative pressure wave effects an outgassing of gas or gas diluted in the liquid medicament and an increase of the size of existing air bubbles. This stimulates the combination of several small air bubbles into one larger air bubble. Larger air bubbles rise up to the top surface of the liquid medicament more easily.

In an embodiment, the mechanical oscillation results from an impulse hammer, a vibration motor, an ultra-sound generator, and/or an ultra-sound sonotrode. These are widely available and cheap devices, which enable removing of gas and/or gas bubbles from a liquid medicament stored in a reservoir.

In an embodiment, the mechanical oscillation results from an infusion pump device having installed the reservoir. In a phase of preparation, the mechanical oscillation can be transmitted to the displacing member in order to generate the mechanical wave in the liquid medicament for removing gas and/or gas bubbles. After the phase of preparation, administering of an amount of the liquid medicament can be performed.

According to this disclosure, an auxiliary device for removing gas and/or gas bubbles from a liquid medicament which is stored in a reservoir for an infusion pump device, wherein the reservoir comprises a displacing member which is at least partly displaceable relative to the reservoir thereby enabling receiving mechanical oscillations in order to generate mechanical waves in the liquid medicament, comprises: an oscillation generator for generating a mechanical oscillation; and a transmission facility for enabling transmission of the mechanical oscillation from the oscillation generator to the displacing member of the reservoir, such that the displacing member can generate a mechanical wave in the liquid medicament for removing gas and/or gas bubbles from the liquid medicament.

In an embodiment, the transmission facility is adapted for enabling transmission of the mechanical oscillation from the oscillation generator to a displacing member which is a plunger displaceably arranged at an opening of the reservoir, such that the plunger can generate a mechanical wave in the liquid medicament for removing gas and/or gas bubbles from the liquid medicament.

In an embodiment, the transmission facility is adapted for enabling transmission of the mechanical oscillation from the oscillation generator to a displacing member which is a flexible membrane which seals an opening of the reservoir, such that the flexible membrane can generate a mechanical wave in the liquid medicament for removing gas and/or gas bubbles from the liquid medicament.

In an embodiment, the oscillation generator includes one or more of: an impulse hammer, a vibration motor, an ultra-sound generator, and an ultra-sound sonotrode.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
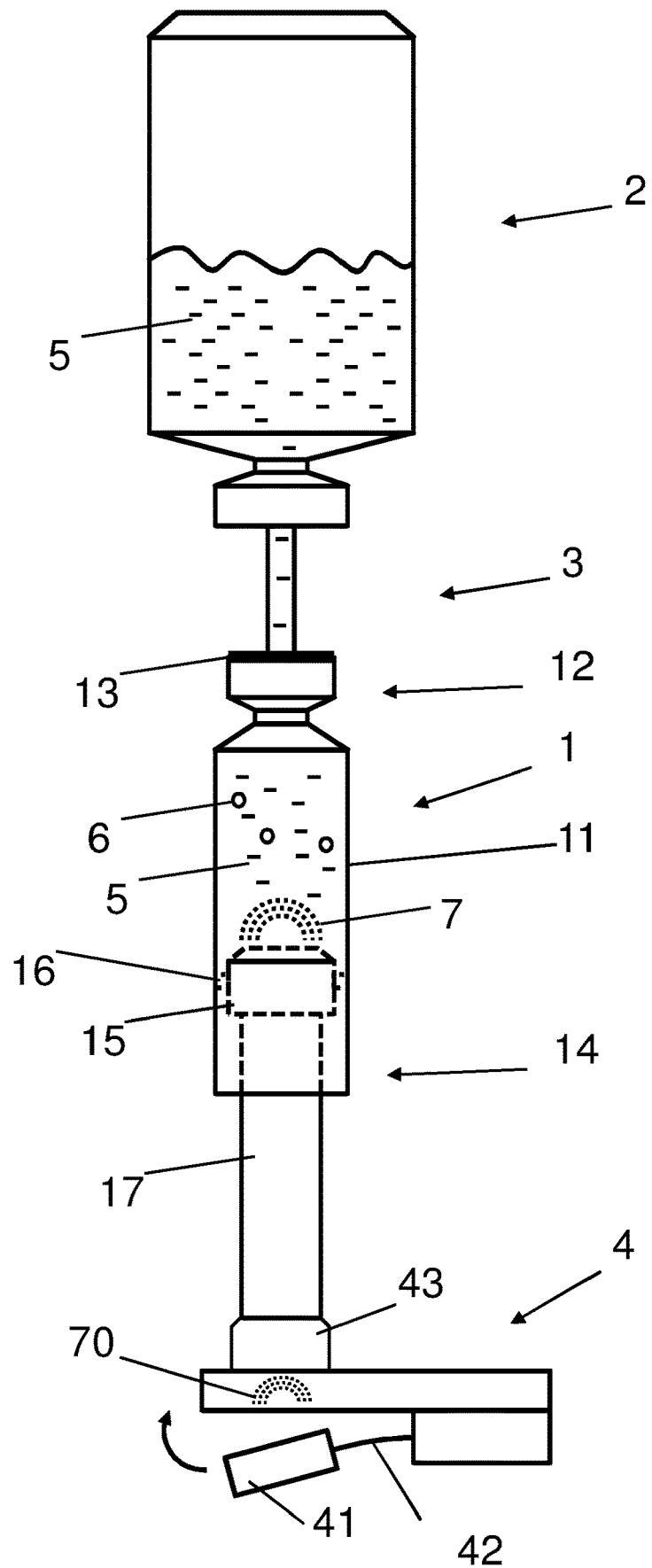
FIG. 1 illustrates schematically a reservoir which has stored a liquid medicament, wherein the reservoir is connected via a transfer appliance to a storage container, wherein the reservoir includes a plunger which is connected via a plunger rod to an oscillation generator, and wherein the plunger rod is connected to an auxiliary device for removing gas and/or gas bubbles from the liquid medicament.

FIG. 1 illustrates schematically a reservoir 1 for an infusion pump device (not shown in FIG. 1), such as an insulin pump. The reservoir 1 is fluidically connected via a transfer appliance 3 to a storage container 2. In some applications, the transfer appliance 3 is also referred to as transfer guard. The storage container 2 has stored a liquid medicament 5. The liquid medicament 5 stored in the storage container 2 is illustrated in FIG. 1 by a plurality of horizontal dashes below a waved line. As illustrated schematically in FIG. 1, the reservoir 1 also has stored an amount of the liquid medicament 5, which has been transferred from the storage container 2 to the reservoir 1. The liquid medicament 5 stored in the reservoir 1 is illustrated schematically by a plurality of horizontal dashes. As illustrated schematically in FIG. 1, the reservoir 1 further comprises gas bubbles 6, which were generated, for example, during the transfer of liquid medicament 5 from the storage container 2 to the reservoir 1. The gas bubbles 6 are illustrated schematically by a plurality of circles.

As illustrated in FIG. 1, a plunger end 14 of the reservoir 1 (illustrated in FIG. 1 on the bottom of the reservoir 1) comprises an opening. The opening is designed for supporting a plunger 15. The plunger 15 is also supported by the reservoir 1 and is movable in an axial direction between the plunger end 14 of the reservoir 1 and a connector end 12 (which will be described below) of the reservoir 1. The plunger 15 typically comprises a sealing element 16 cooperating between the plunger 15 and a shell 11 of the reservoir 1 and providing a fluid tight sealing while enabling movability of the plunger 15 in axial direction. The plunger 15 is connected to a plunger rod 17 for moving the plunger 15 in axial direction. The plunger 15 has the design of a displaceable member which enables transmission of mechanical oscillations to the liquid medicament 5. The plunger 15 can receive mechanical oscillations in order to generate mechanical waves in the liquid medicament 5.

As illustrated in FIG. 1, the connector end 12 of the reservoir 1 (illustrated in FIG. 1 on the top of the reservoir 1) is designed for connecting the transfer appliance 3. The connector end 12 is further designed for connection with an infusion pump device thereby enabling administration of the liquid medicament 5 to a patient, for example via an infusion set. The connector end 12 of the reservoir 1 comprises an opening which is sealed with a flexible membrane 13, such as a septum. A region in the center of the flexible membrane 13 has the design of a displaceable member which enables transmission of mechanical oscillations to the liquid medicament 5. The flexible membrane 13 can receive mechanical oscillations in order to generate mechanical waves in the liquid medicament 5.

In some embodiments, the reservoir 1 and/or the plunger 15 have a cylindrical design. In some embodiments, the plunger 15 is displaceable in an axial direction of the reservoir 1.

In some embodiments, the reservoir 1 or the shell 11 of the reservoir 1 is manufactured out of glass.

As illustrated in FIG. 1, an end of the plunger rod 17 on the opposite side of the plunger 15 is connected to an auxiliary device 4. In the embodiment schematically illustrated in FIG. 1, the auxiliary device 4 comprises an oscillation generator 41, 42, which includes a hammer element 41 which is deflectably supported by a spring element 42. The hammer element 41 has the design of an impulse hammer. The hammer element 41 can be deflected and released in such a manner that after releasing the hammer element 41, the spring element 42 accelerates the hammer element 41, wherein the hammer element 41 impacts onto a surface of the auxiliary device 4. Due to the impact, a mechanical oscillation 70 is generated in the auxiliary device 4. As illustrated schematically in FIG. 1, a transmission facility 43 of the auxiliary device 4 enables transmission of the mechanical oscillation 70 from the auxiliary device 4 via the plunger rod 17 to the plunger 15. The plunger 15 receives the mechanical oscillation and generates a mechanical wave 7 in the liquid medicament 5 stored in the reservoir 1, as illustrated in FIG. 1. The mechanical wave 7 propagates in the liquid medicament 5, thereby effecting that the gas bubbles 6 in the reservoir 1 rise up towards the connector end 12.

In the step of separation effected by the mechanical oscillation 70 of the auxiliary device 4, which is transmitted from the auxiliary device 4 via the transmission facility 43 to the plunger rod 17 and to the plunger 15, a mechanical wave 7 is generated in the liquid medicament 5, wherein the mechanical wave 7 propagates in the liquid medicament, and wherein the gas bubbles 6 are separated from the liquid medicament 5.

Thereafter, in a step of back transfer, gas collected by separating gas bubbles 6 from the liquid medicament 5 can be transferred back to the storage container 2 (or elsewhere) by moving the plunger 15 in axial direction towards the connector end 12 of the reservoir 1.

The mechanical oscillation 70 generated by the auxiliary device 4 is transmitted in axial direction via the plunger rod 17 to the plunger 6. Accordingly, the plunger 15 oscillates in axial direction. Because the plunger 15 is displaceable relative to the reservoir 1 (in axial direction), transmission of the mechanical oscillation 70 to the reservoir 1 is only possible via friction forces between the plunger 15 and the reservoir 1. Furthermore, transmission of the mechanical oscillation 70 to the reservoir 1 is additionally reduced by the sealing element 16 arranged between the plunger 15 and the shell 11 of the reservoir 1. The sealing element 16 can be manufactured out of a suitable flexible material having a predefined elasticity in order to reduce transmission of oscillations to the reservoir 1 even further. Accordingly, by performing the step of separation using the auxiliary device 4 as described above, mechanical stress to the reservoir 1 is reduced and the risk of micro-cracks in the reservoir 1 is thereby reduced.

As illustrated in FIG. 1, the transmission facility 43 of the auxiliary device 4 is adapted for enabling transmission of the mechanical oscillation 70 from the oscillation generator 41, 42 via the plunger rod 17 to the plunger 15, such that the plunger 15 generates a mechanical wave 7 in the liquid medicament 5 for removing gas and/or gas bubbles 6 from the liquid medicament 5. In order to enable transmission of the mechanical oscillation 70, the transmission facility 43 can include a mechanical coupling for firmly coupling the auxiliary device 4 to the plunger rod, for example a snap mechanism, a screwed joint, etc.

In an embodiment, which is not illustrated in FIG. 1, the transmission facility 43 of the auxiliary device 4 is adapted for enabling transmission of the mechanical oscillation 70 from the oscillation generator 41, 42 to the flexible membrane 13, such that the flexible membrane 13 generates a mechanical wave 7 in the liquid medicament for removing gas and/or gas bubbles 6 from the liquid medicament. In order to enable transmission of the mechanical oscillation 70, the transmission facility 43 can include a transmission device adapted to the flexible membrane 13, such as a sonotrode, a horn, etc.

In the embodiment illustrated in FIG. 1, the mechanical oscillation 70 is the result of a mechanical stroke and the mechanical oscillation 70 has the form of an impulse.

In some embodiments, which are not illustrated in FIG. 1, the mechanical oscillation results from a vibration motor, an ultra-sound generator, and/or an ultra-sound sonotrode.

In some embodiments, which are not illustrated in FIG. 1, the reservoir 1 can be arranged in an infusion pump device and the mechanical oscillation 70 can be generated by the infusion pump device. In a phase of preparation, the mechanical oscillation 70 can be transmitted to the plunger in order to generate the mechanical wave 7 in the liquid medicament 5 for removing gas and/or gas bubbles 6. After the phase of preparation, administering of an amount of the liquid medicament 5 can be performed.

Instead of moving the plunger 15 slowly in axial direction, as is the case when filling the reservoir 1 or when administering liquid medicament 5 to a patient, the mechanical oscillation 70 generated in the auxiliary device 4 effects a highly dynamic motion of the plunger 15. The shell 11 of the reservoir 1 remains completely free from mechanical stress, because the motion of the plunger 15 effected by the mechanical oscillation 70 is in the axial direction.

The wave 7 generated in the liquid medicament 5 propagates through the liquid medicament 5 because of the incompressibility of the liquid.

The wave 7 generated in the liquid medicament 5 can be in the form of a positive pressure wave. A positive pressure wave effects that gas and/or gas bubbles sticking to the shell 11 of the reservoir 1 can be detached from the shell 11 and therefore can rise to the top surface of the liquid medicament 5.

The wave 7 generated in the liquid medicament 5 can be in the form of a negative pressure wave. A negative pressure wave effects an outgassing of gas or gas diluted in the liquid medicament 5 and an increase of the size of existing air bubbles 6. This stimulates the combination of several small air bubbles into one larger air bubble. Larger air bubbles rise up to the top surface of the liquid medicament 5 more easily.

Figure 2:
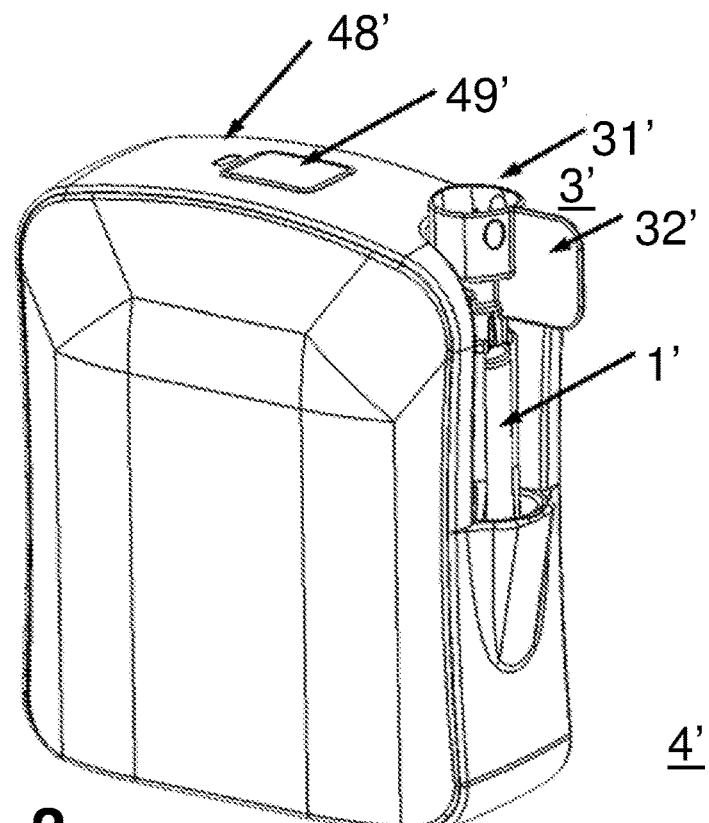
FIG. 2 illustrates schematically an embodiment of an auxiliary device for removing gas and/or gas bubbles from a liquid medicament which is stored in a reservoir for an infusion pump device for an infusion pump device.

FIG. 2 illustrates schematically an embodiment of an auxiliary device 4' for removing gas and/or gas bubbles from a liquid medicament which is stored in a reservoir 1' for an infusion pump device. The auxiliary device 4' includes a housing which is configured to receive the reservoir 1'. As illustrated in FIG. 2, the reservoir 1' is connected to a transfer appliance 3'. The transfer appliance 3' includes a holding fixture 31' for holding a storage container (not shown in FIG. 2). The transfer appliance 3' includes a handle 32' enabling that the patient can safely hold the transfer appliance 3'. As illustrated in FIG. 2, the housing of the auxiliary device 4' includes a control element 49' for controlling operation of the auxiliary device 4' and a status indicator 48', such as a light emitting diode, for indicating, for example, if the auxiliary device 4' is operating or not.

Figure 3:
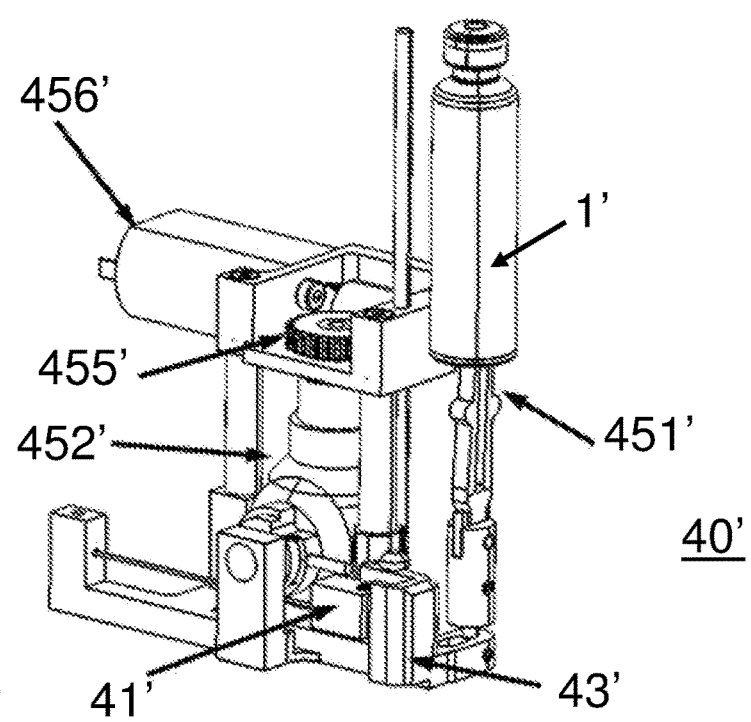
FIG. 3 illustrates schematically an embodiment of an actuating mechanism of the auxiliary device illustrated in FIG. 2.

FIG. 3 illustrates schematically an embodiment of an actuating mechanism 40' of the auxiliary device 4' illustrated in FIG. 2. The actuating mechanism 40' includes a hammer element 41' and a transmission facility 43'. The transmission facility 43' is connected to a piston coupling element 451' for connection to a reservoir 1'. As illustrated in FIG. 3, the actuating mechanism 40' includes a free-wheel clutch 452' which is connected to a gear reduction 455' which is further connected to an electrical motor 456'.

Figure 4:
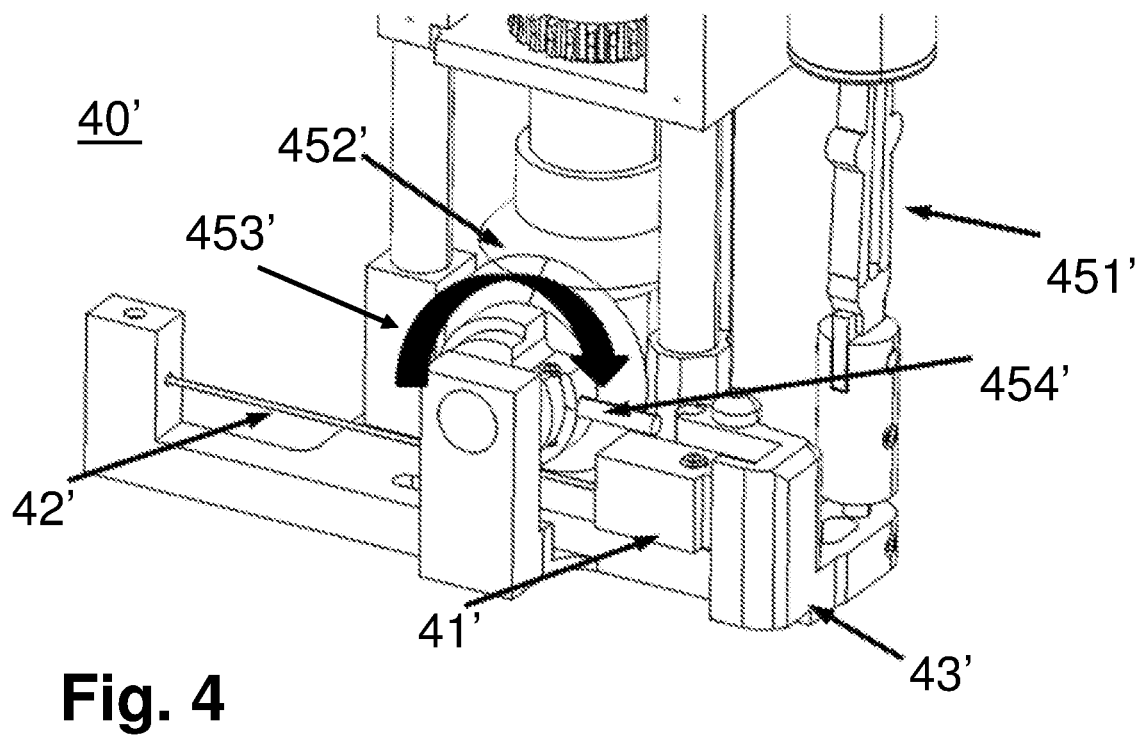
FIG. 4 illustrates schematically an enlarge view of the actuating mechanism illustrated in FIG. 3.

FIG. 4 illustrates schematically an enlarged view of the actuating mechanism 40' illustrated in FIG. 3. The actuating mechanism 40' further includes a spring element 42'. The spring element 42' has the design of a flexible rod. The spring element 42' is connected to the hammer element 41' on one side and is connected to a basis structure of the actuating mechanism 40' on the other side. The spring element 42' enables the hammer element 41' to be displaced with respect to the transmission facility 43'. The spring element 42' further enables that after displacement and release of the hammer element 41', the hammer element 41' can be accelerated in order to impact with the transmission facility 43', such that a mechanical oscillation is induced, wherein the mechanical oscillation is transmitted via the piston coupling element 451' to the plunger of the reservoir 1' in order to generate a mechanical wave in the liquid stored in the reservoir 1'.

As illustrated in FIG. 4, the actuating mechanism 40' includes a driving pin 454'. The driving pin 454' is driven by the free-wheel clutch as indicated in FIG. 4 by a turning direction 453'. The driving pin 454' effects a displacement and release of the hammer element 41', wherein after release the hammer element 41' impacts with the transmission facility 43' as described above.

In one turning direction, the electrical motor 456' causes the plunger of the reservoir 1' to move downwards. In the other turning direction, the electrical motor 456' moves the plunger of the reservoir 1' upwards. When the plunger moves downwards, liquid medicament flows from a storage container (not shown in FIGS. 2-4) into the reservoir 1'. When the plunger moves upwards, a volume flows from the reservoir 1' into the storage container. When the plunger moves upwards, gas above the surface of the liquid medicament stored in the reservoir 1' can be transferred from the reservoir 1' into the storage container (not shown in FIGS. 2-4). Gas bubbles which adhere to the plunger or to the shell (from the inside) of the reservoir 1' cannot be removed by this procedure.

In order to remove gas bubbles contained in the liquid medicament stored in the reservoir 1', the actuating mechanism is designed such that when the plunger is moved upwards, the hammer element 41' is actuated via the free-wheel clutch 452' and the driving pin 454', such that mechanical waves are generated in the reservoir 1' via the plunger.

The auxiliary device 4' enables filling the reservoir 1' with liquid medicament including the following steps:

Step 1. The reservoir is inserted into the auxiliary device 4', wherein the plunger is on the bottom end and the reservoir is filled with gas respectively with air.

Step 2. The storage container is connected to the reservoir via the transfer appliance 3'.

Step 3. The plunger is moved upwards. Gas respectively air is pushed into the storage container. Periodically, a mechanical oscillation is generated because of the free-wheel clutch, the driving pin 454' and the hammer element 41'. However, at this stage the mechanical oscillation has no effect.

Step 4. The plunger is moved downwards in order to transfer a partial amount of liquid medicament from the storage container into the reservoir 1'.

Step 5. The plunger is moved upwards again a fraction of the movement of the previous step, wherein mechanical waves are generated in the liquid medicament and such that gas bubbles can raise to the surface of the liquid medicament of the reservoir 1' and such that gas above the surface can be transferred back to the storage container.

Step 6, Step 4, and Step 5 are repeated several times until the reservoir 1' is filled with the liquid medicament.

Step 7. The reservoir 1' is withdrawn from the auxiliary device 4', the reservoir 1' is disconnected from the storage container and the transfer appliance and is ready to be inserted into an infusion pump device.

The auxiliary device 4' according to FIGS. 2-4 can include a battery or similar for providing electrical power for the electrical motor 456' and possibly for a controller controlling operation of the auxiliary device 4'.

Figure 5:
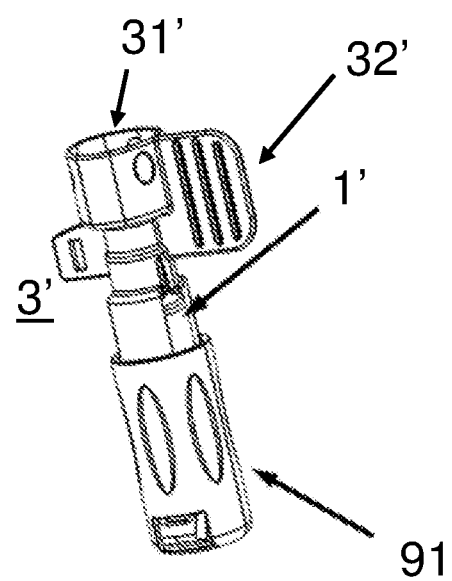
FIG. 5 illustrates schematically a reservoir connected to a transfer appliance and arranged within a cylindrical handling device.

FIG. 5 illustrates schematically a reservoir 1' connected to a transfer appliance 3' and arranged within a cylindrical handling device 91. The cylindrical handling device 91 is configured for moving the plunger inside the reservoir 1'.

Figure 6:
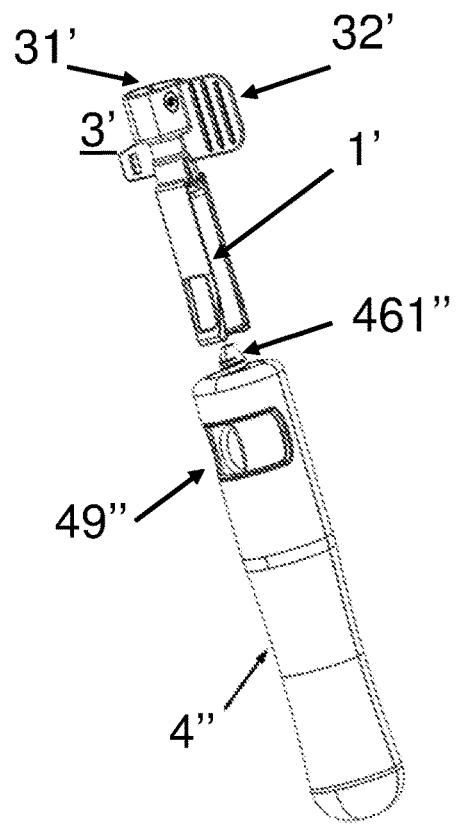
FIG. 6 illustrates schematically a reservoir connected to a transfer appliance which are arranged for insertion into another embodiment of an auxiliary device for removing gas and/or gas bubbles from a liquid medicament which is stored in a reservoir for an infusion pump device for an infusion pump device.

FIG. 6 illustrates schematically a reservoir 1' connected to a transfer appliance 3' which are arranged for insertion into another embodiment of an auxiliary device 4" for removing gas and/or gas bubbles from a liquid medicament which is stored in a reservoir for an infusion pump device for an infusion pump device. The auxiliary device 4" includes a control element 49", which will described further below, and a plunger coupling element 461' for coupling the auxiliary device 4' with the plunger of the reservoir 1'.

The auxiliary device 4" illustrated in FIG. 6 and further described below has a mechanical design and does not require a battery or similar.

Figure 7:
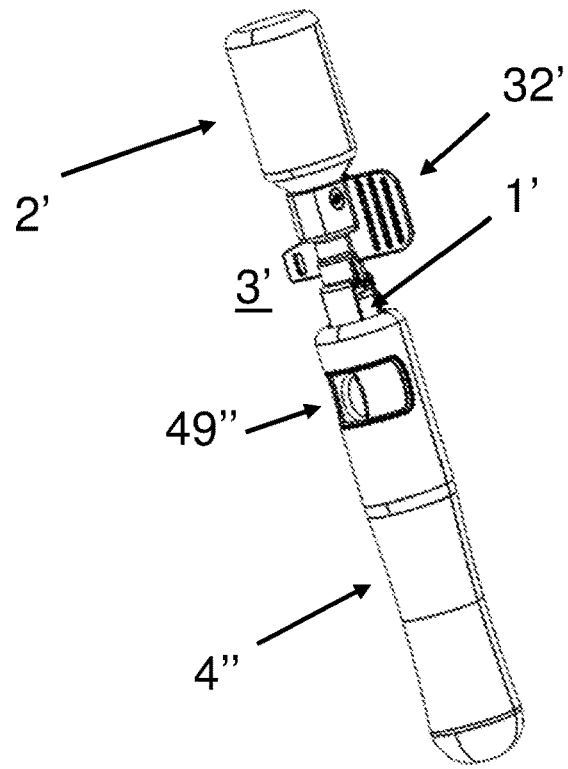
FIG. 7 illustrates schematically a storage container connected via a transfer appliance to a reservoir which is inserted into connected with an embodiment of an auxiliary device for removing gas and/or gas bubbles from a liquid medicament which is stored in a reservoir for an infusion pump device for an infusion pump device.

FIG. 7 illustrates schematically a storage container 2' connected via a transfer appliance 3' to a reservoir 1' which is inserted into and connected with an embodiment of an auxiliary device 4" for removing gas and/or gas bubbles from a liquid medicament which is stored in a reservoir for an infusion pump device.

The auxiliary device 4" illustrated in FIG. 7 is configured such that the patient can move the plunger inside the reservoir 1' in order to transfer liquid medicament from the storage container 2' to the reservoir 1'.

The control element 49' serves for removing gas bubbles from the reservoir 1'. The control element 49' transmits a mechanical oscillation to the plunger of the reservoir 1' and generates a mechanical wave in the liquid medicament stored in the reservoir 1'. Using the auxiliary device 4", the patient can transfer gas accumulated above the surface of the liquid medicament from the reservoir 1' to the storage container 2'.

Figure 8:
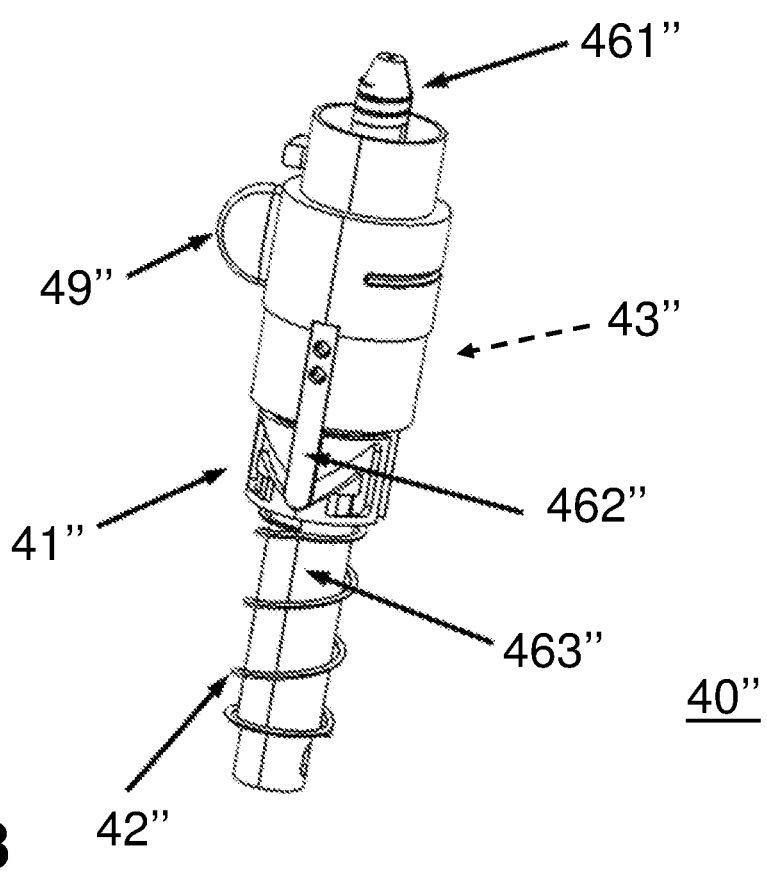
FIG. 8 illustrates an embodiment of an actuating mechanism of the auxiliary device illustrated in FIG. 6 and FIG. 7.

FIG. 8 illustrates an embodiment of an actuating mechanism 40" of the auxiliary device 4" illustrated in FIG. 6 and FIG. 7. The actuating mechanism 40" includes the control element 49'. The actuation mechanism 40" further includes a hammer element 41", which has a cylindrical design and includes guiding grooves for a flexible guiding pin 462' connected to a basis structure of the actuating mechanism 40'. Preferably, a pair of guiding grooves are included enabling that the control element 49' can be manipulated in either direction such that left hand or right hand operation of the control element 49' is possible equally well. The actuating mechanism 40" includes a bearing shaft 463' and a spring element 42". The spring element 42" has a coil spring design and is arranged along the bearing shaft 463'.

By manipulating the control 49', the hammer element 41" is moved downwards along the bearing shaft 463" until the flexible guiding pin 462' jumps out of a guiding groove and thereby releases the hammer element 41", which is accelerated by the spring element 42" upwards until the hammer element 41" impacts on a basis structure of the actuation mechanism 40". The impact generates a mechanical oscillation which is transferred via the plunger coupling element 461' to the plunger of the reservoir 1', wherein a mechanical wave is generated in the liquid medicament stored in the reservoir 1', thereby removing gas and/or gas bubbles from the liquid medicament.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

| | |
|---|---|
| 1, 1' | reservoir |
| 11 | shell |
| 12 | connector end of reservoir |
| 13 | flexible membrane |
| 14 | plunger end of reservoir |
| 15 | plunger |
| 16 | sealing element |
| 17 | plunger rod |
| 2 | storage container |
| 3, 3' | transfer appliance |
| 31' | holding fixture |
| 32' | handle |
| 4, 4', 4" | auxiliary device |
| 40', 40" | actuating mechanism |
| 41, 41', 41" | hammer element |
| 42, 42', 42" | spring element |
| 43, 43' | transmission facility |
| 451' | plunger coupling element |
| 452' | free-wheel clutch |
| 453' | turning direction |
| 454' | driving pin |

LIST OF REFERENCE NUMERALS

| | |
|---|---|
| 455' | gear reduction |
| 456' | electrical motor |
| 461' | plunger coupling element |
| 462' | flexible guiding pin |
| 463' | bearing shaft |
| 48' | status indicator |
| 49', 49" | control element |
| 5 | liquid medicament |
| 6 | gas bubbles |
| 7 | mechanical wave |
| 70 | mechanical oscillation |
| 91 | cylindrical handle device |

What is claimed is:

1. A method for removing gas and/or gas bubbles from a liquid medicament used in an infusion pump, the method comprising:
providing a reservoir containing liquid medicament and providing a displacing member that is at least partly displaceable relative to the reservoir;
providing a mechanical actuator configured to generate a mechanical oscillation; and
using the mechanical actuator to cause a mechanical impact to thereby transmit a mechanical oscillation to the displacing member and thereby generating a mechanical wave in the liquid medicament, wherein the wave removes gas and/or gas bubbles from the liquid medicament.

2. The method according to claim 1, wherein the displacing member is a plunger arranged at an opening of the reservoir, and wherein the mechanical oscillation is transmitted to the plunger, which generates the mechanical wave.

3. The method according to claim 2, wherein the plunger comprises a sealing element.

4. The method according to claim 2, wherein a plunger rod is connected to the plunger, and wherein the mechanical oscillation is transmitted to the plunger via the plunger rod.

5. The method according to claim 1, wherein the displacing member is a flexible membrane which seals an opening of the reservoir, and wherein the mechanical oscillation is transmitted to the flexible membrane.

6. The method according to claim 1, wherein the reservoir is cylindrical and the displacing member is displaceable in an axial direction of the reservoir.

7. The method according to claim 1, wherein the mechanical oscillation has the form of an impulse and/or is the result of a mechanical stroke.

8. The method according to claim 1, wherein the mechanical wave generated by the displacing member has the form of a positive pressure wave.

9. The method according to claim 1, wherein the mechanical wave generated by the displacing member has the form of a negative pressure wave.

10. The method according to claim 1, wherein the mechanical oscillation results from an impulse hammer.

11. A device for removing gas and/or gas bubbles from a liquid medicament, comprising:
a reservoir for an infusion pump;
a displacing member which is at least partly displaceable relative to the reservoir and is configured to receive mechanical oscillations in order to generate mechanical waves in the liquid medicament;
a mechanical actuator configured for causing a mechanical impact to thereby generate the mechanical oscillations; and a transmission configured to transmit the mechanical oscillations from the mechanical actuator to the displacing member, whereby the displacing member is configured to generate a mechanical wave in the liquid medicament for removing gas and/or gas bubbles from the liquid medicament.

12. The device according to claim 11, wherein the displacing member is a plunger displaceably arranged at an opening of the reservoir.

13. The device according to claim 11, wherein the displacing member is a flexible membrane which seals an opening of the reservoir.

14. The auxiliary device according to claim 11, wherein the mechanical actuator comprises an impulse hammer.

15. A method for removing gas and/or gas bubbles from a liquid medicament used in an infusion pump, the method comprising:
- providing a reservoir containing liquid medicament and providing a displacing member that is at least partly displaceable relative to the reservoir;
- providing a flexible membrane configured to receive oscillations and further configured to transmit the oscillations to the liquid medicament to remove gas and/or gas bubbles from the liquid medicament;
- providing a mechanical actuator configured to generate a mechanical oscillation; and
- using the mechanical actuator to transmit a mechanical oscillation to the displacing member and thereby generating a mechanical wave in the liquid medicament, wherein the wave removes gas and/or gas bubbles from the liquid medicament.

\* \* \* \* \*